United States Patent
Bayer et al.

(10) Patent No.: US 9,024,016 B2
(45) Date of Patent: May 5, 2015

(54) PROCESS FOR PRODUCING ACESULFAME POTASSIUM

(71) Applicant: Nutrinova Nutrition Specialties & Food Ingredients GmbH, Sulzbach (DE)

(72) Inventors: Michael J. Bayer, Eschborn (DE); Stephan Brietzke, Wiesbaden (DE); Peter Groer, Babenhausen (DE); Christoph Mollenkopf, Frankfurt am Main (DE)

(73) Assignee: Nutrinova Nutrition Specialists & Food Ingredients GmbH, Sulzbach (DE)

( * ) Notice: Subject to any disclaimer, the term of this patent is extended or adjusted under 35 U.S.C. 154(b) by 0 days.

(21) Appl. No.: 13/901,735

(22) Filed: May 24, 2013

(65) Prior Publication Data

US 2013/0331565 A1    Dec. 12, 2013

Related U.S. Application Data

(60) Provisional application No. 61/657,231, filed on Jun. 8, 2012.

(51) Int. Cl.
| | |
|---|---|
| *C07D 291/06* | (2006.01) |
| *C07D 307/02* | (2006.01) |
| *A23L 1/236* | (2006.01) |
| *C07C 307/02* | (2006.01) |

(52) U.S. Cl.
CPC ............... *A23L 1/236* (2013.01); *C07D 291/06* (2013.01); *C07C 307/02* (2013.01)

(58) Field of Classification Search
USPC .......................................................... 544/2
See application file for complete search history.

(56) References Cited

U.S. PATENT DOCUMENTS

| | | |
|---|---|---|
| 5,084,180 A | 1/1992 | Boateng |
| 5,744,010 A | 4/1998 | Roscher et al. |
| 5,808,159 A | 9/1998 | Giebeler |
| 7,977,514 B2 | 7/2011 | Peters et al. |
| 2003/0065218 A1 | 4/2003 | Mollenkopf |
| 2009/0318685 A1 | 12/2009 | Saito |
| 2010/0274057 A1 | 10/2010 | Peters et al. |
| 2011/0256045 A1 | 10/2011 | Brietzke et al. |
| 2011/0256046 A1 | 10/2011 | Brietzke et al. |

FOREIGN PATENT DOCUMENTS

| | | |
|---|---|---|
| CN | 1883790 | 12/2006 |
| DE | 3522470 | 1/1987 |
| DE | 3545196 | 6/1987 |
| JP | 54032406 | 3/1979 |

OTHER PUBLICATIONS

Linkies et al. Synthesis (1990), (5), 405-6.*
Suenaga, T., "Ethylene-amine salt recovery—by converting the hydrochloride into the sulphate, and reacting with ammonia in aq. Solvent to ppte. Ammonium sulphate", WPI/Thompson, vol. 1979, No. 16, XP 002598345 (See JP54032406).

* cited by examiner

*Primary Examiner* — Kahsay Habte

(57) ABSTRACT

In one embodiment, the invention relates to processes for producing acesulfame potassium. In one embodiment, the process comprises the step of reacting a first reaction mixture to form an amidosulfamic acid salt such as a trialkyl ammonium amidosulfamic acid salt. The first reaction mixture comprises sulfamic acid, an amine, and smaller amounts, if any, acetic acid, e.g., less than 1 wt % (10000 wppm). In terms of ranges, the first reaction mixture may comprise from 1 wppm to 1 wt % acetic acid. The process further comprises the step of reacting the amidosulfamic acid salt with diketene to form an acetoacetamide salt. In preferred embodiments, the amidosulfamic acid salt formation reaction is conducted at pH levels from 5.5 to 7.0. The process further comprises the step of deriving the acesulfame-K from the acetoacetamide salt.

11 Claims, 1 Drawing Sheet

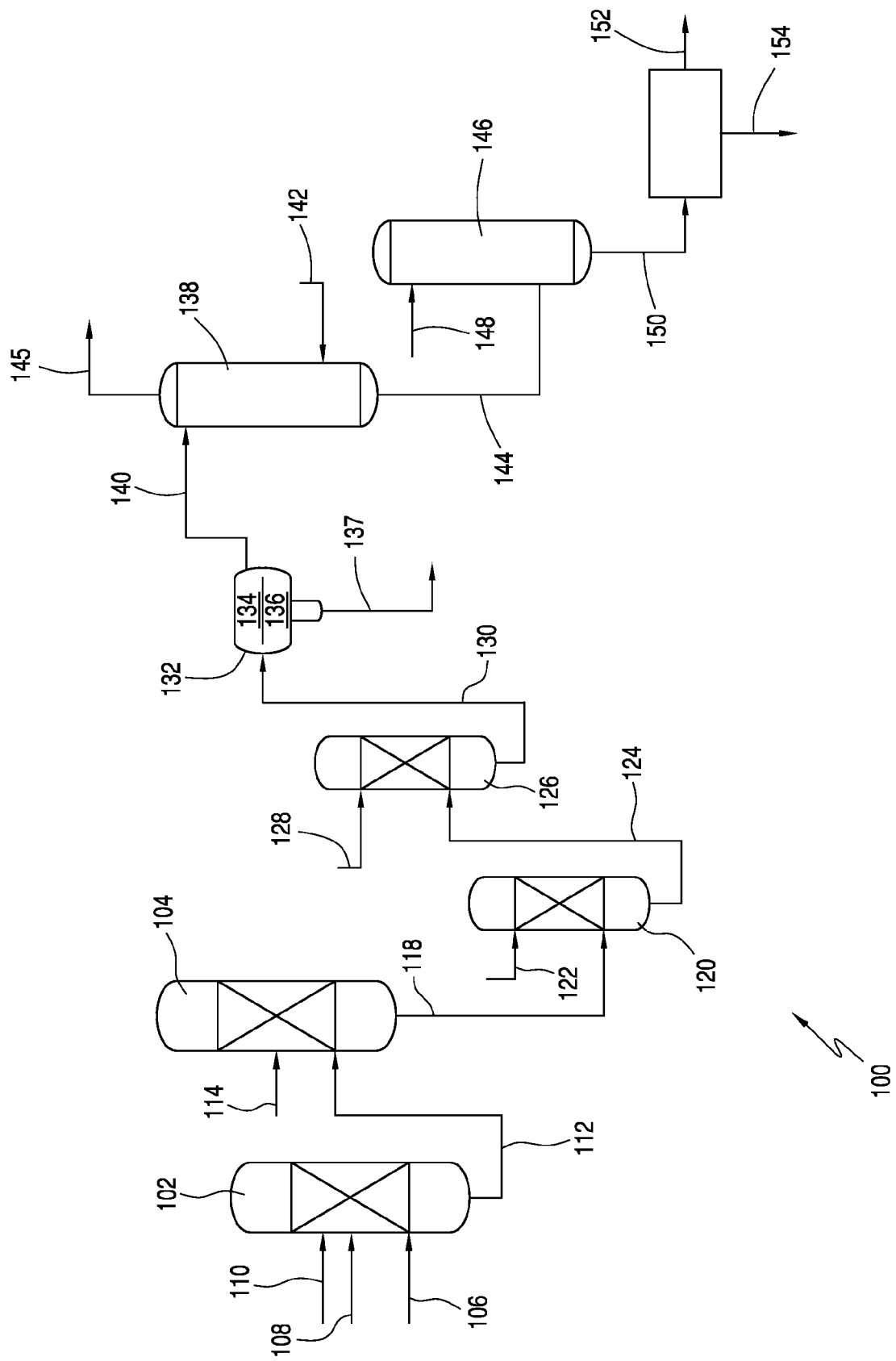

US 9,024,016 B2

PROCESS FOR PRODUCING ACESULFAME POTASSIUM

CROSS REFERENCE TO RELATED APPLICATIONS

This application is a non-provisional of and claims priority to U.S. Provisional Application No. 61/657,231, which was filed on Jun. 8, 2012. The entirety of this application is incorporated by reference herein.

FIELD OF INVENTION

The present invention relates generally to the production of acesulfame potassium. More specifically, the present invention relates to the production of acesulfame potassium and/or acesulfame potassium intermediates having low yellowing indices.

BACKGROUND OF THE INVENTION

Acesulfame potassium ("Acesulfame-K") has an intense, sweet taste and has been used in many food-related applications. In conventional acesulfame-K production processes, sulfamic acid and an amine, e.g., triethyleamine, are reacted to form an amidosulfamic acid salt. As one example, the amidosulfamic acid salt may be a trialkyl ammonium amidosulfamic acid salt. The amidosulfamic acid salt may then be reacted with diketene to form an acetoacetamide salt. The acetoacetamide salt may be cyclized, hydrolyzed, and neutralized to form the Acesulfame-K. U.S. Pat. No. 5,744,010 discloses an exemplary acesulfame-K production process.

Typically, to initiate and efficiently maintain the reaction under production-scale conditions, acetic acid is added to the sulfamic acid and amine. The acetic acid may form a corresponding ammonium acetate salt, which may promote the acetoacetylation reaction that forms the acetoacetamide salt. The sulfamic acid (and in some cases acetic acid) create acidic reaction conditions, which may drive down pH of the reaction mixtures, e.g., to a pH level less than 5.5. In some cases, e.g., to create a more neutral environment, amine may be added to the reaction in amounts greater than the stoichiometric amounts, e.g., the reaction is conducted in an excess of amine. This use of excess amine and the accompanying increase in pH, however, may cause coloration problems in the resultant acetoacetamide salt.

Even in view of the conventional processes, the need exists for an improved acesulfame-K production process that utilizes smaller amounts of reactants, e.g., acetic acid and/or amine, and produces a high quality acesulfame-K product at improved yield rates.

All of the references discussed above are hereby incorporated by reference.

SUMMARY OF THE INVENTION

The present invention relates to processes for producing acesulfame potassium. In one embodiment, the process comprises the step of reacting a first reaction mixture to form an amidosulfamic acid salt such as a trialkyl ammonium amidosulfamic acid salt. The first reaction mixture comprises sulfamic acid, an amine, e.g., triethylamine, and smaller amounts, if any, acetic acid, e.g., less than 1 wt % (10000 wppm). In terms of ranges, the first reaction mixture may comprise from 1 wppm to 1 wt % acetic acid. The process further comprises the step of reacting the amidosulfamic acid salt with diketene to form an acetoacetamide salt. In preferred embodiments, the amidosulfamic acid salt formation reaction is conducted at pH levels from 5.5 to 7.0. The process further comprises the step of deriving the acesulfame-K from the acetoacetamide salt, which may comprise the steps of reacting the acetoacetamide salt with a cyclizing agent to form a cyclic sulfur trioxide adduct and deriving the acesulfame potassium composition from the cyclic sulfur trioxide adduct. The deriving may comprise hydrolyzing the cyclic sulfur trioxide adduct to form acesulfame-H and neutralizing the acesulfame-H with potassium hydroxide to form the potassium acesulfame. In one embodiment, a molar ratio of acetic acid to sulfamic acid in the first reaction mixture is less than 0.095:1. A molar ratio of amine to sulfamic acid in the first reaction mixture may be less than 1.06:1. The reaction may be conducted at an amine excess of less than 6 mol %. In one embodiment, the amidosulfamic acid salt may have a yellowing index less than 5 and/or the acetoacetamide salt may have a yellowing index less than 45. The acesulfame potassium may have a yellowing index less than 5. In one embodiment, the process does not comprise an acetic acid removal step. The reaction of the amidosulfamic acid salt with diketene may comprise contacting the amidosulfamic acid salt and diketene to form a second reaction mixture and reacting the second reaction mixture to form the acetoacetamide salt. Also disclosed are acesulfame potassium, amidosumfamic acid salt, and acetoacetamide salt produced by the process. In some embodiments, the invention relates to a process for producing an amidosulfamic acid salt comprising the step of reacting sulfamic acid, an amine and less than 10000 wppm acetic acid to form the amidosulfamic acid salt. The reacting may be conducted at a pH ranging from 5.5 to 7.0. In some embodiment, the invention relates to a process for producing an acetoacetamide salt comprising the steps of reacting sulfamic acid, an amine and from 1 wppm to 10000 wppm acetic acid to form an amidosulfamic acid salt reacting the amidosulfamic acid salt with diketene to form the acetoacetamide salt. In one embodiment, the amidosulfamic acid salt has a yellowing index less than 5 and/or the acetoacetamide salt has a yellowing index less than 45.

BRIEF DESCRIPTION OF THE DRAWINGS

The invention is described in detail below with reference to the appended drawings.

FIG. 1 is a process flow sheet of an acesulfame-K production process in accordance with one embodiment of the present invention.

DETAILED DESCRIPTION OF THE INVENTION

Introduction

Conventional processes for producing acesulfame-K react sulfamic acid, an amine and acetic acid to form an amidosulfamic acid salt. Typically, under production-scale conditions, the acetic acid is added to the sulfamic acid and amine to initiate and efficiently maintain the reaction. As such, the acetic acid is typically present in higher amounts, e.g., greater than 1 wt %, based on the total weight of the reactants in the reaction mixture (not including solvent). If solvent is included in the weight percentage calculation, the acetic acid typically may be present in an amount greater than 0.15 wt %. The reaction is usually conducted in excess of amine, which drives up the pH at which the reaction is conducted. The amidosulfamic acid salt is then reacted with an acetoacetylating agent, e.g, diketene, to form an acetoacetamide salt.

The use of excess amine and the accompanying increase in pH has been found to cause coloration problems in the resultant acetoacetamide salt.

It has now been discovered that, in contrast to conventional processes, the use of lower amounts (if any) of acetic acid in the amidosulfamic acid salt formation reaction can effectively initiate and maintain the reaction. The reaction then may be conducted using smaller amounts of amine, e.g., lesser excesses. In one embodiment, the amidosulfamic acid salt formation reaction may be conducted at a pH levels ranging from 5.5 to 7.0. As a result, both the yield and the color properties of the resultant acetoacetamide salt may be improved. Also, because the amount of additional acetic acid added to the reaction may be reduced or eliminated, smaller amounts of raw materials can be used to form the same amount of product, which result in additional process efficiencies. In addition, the process components that are required to provide acetic acid and/or amine, e.g., tanks, lines, pumps, etc., may advantageously be reduced or eliminated, resulting in lower capital costs.

Acesulfame-K Formation

The present invention relates to processes for producing acesulfame-K. In one embodiment, the process comprises the step of reacting a reaction mixture, e.g., a first reaction mixture, to form an amidosulfamic acid salt, e.g., a trialkyl ammonium amidosulfamic acid salt. The first reaction mixture comprises sulfamic acid, amine, and lower amounts (if any) of acetic acid. In a preferred embodiment, the first reaction mixture comprises acetic acid in amounts less than 1 wt %, e.g., less than 900 wppm, less than 800 wppm, less than 500 wppm, or less than 100 wppm, based on the total weight of the reactants in the reaction mixture (not including solvent). In terms of ranges, the first reaction mixture may comprise from 1 wppm to 1 wt % acetic acid, e.g., from 1 wppm to 900 wppm, from 1 wppm to 800 wppm, from 1 wppm to 500 wppm, from 10 wppm to 1 wt %, from 10 wppm to 900 wppm, from 10 wppm to 800 from, from 10 wppm to 500 wppm, from 100 wppm to 1 wt %, wppm, from 100 wppm to 900 wppm, from 100 wppm to 800 wppm, or from 100 wppm to 500 wppm. In one embodiment, the first reaction mixture is substantially free of acetic acid, e.g., acetic acid is beneficially eliminated as a reactant. Typically, the acetic acid is added to the sulfamic acid and the amine to initiate and efficiently maintain the reaction under production-scale conditions. In some laboratory conditions, e.g., small-scale batch operations, the rate at which the reaction is initiated is not affected by production constraints. As such, in these small-scale batch operations, it may be unnecessary to add acetic acid. Under conventional production-scale processes, however, higher amounts of acetic acid are typically utilized in the reaction mixture. When solvent is included in the weight percentage calculation, the first reaction mixture may comprise acetic acid in amounts less than 0.175 wt %, e.g., less than 0.15 wt %, less than 0.10 wt %, less than 0.08 wt %, or less than 0.05 wt %. In terms of ranges, the first reaction mixture may comprise from 1 wppm to 150 wppm acetic acid, e.g., from 1 wppm to 100 wppm, from 1 wppm to 80 wppm, or from 1 wppm to 50 wppm.

The lower amounts of acetic acid employed in the present invention advantageously reduce raw material cost. Also, in conventional processes, because higher amounts of acetic acid are used, acetic acid removal steps are often required to provide a purified acesulfame-K intermediate, e.g., the amidosulfamic acid salt and/or the acetoacetamide salt. The lower levels of acetic acid employed in the present invention result in the reduction or elimination of the need for a separate acetic acid removal step during the formation of the acesulfame-K intermediates.

As noted above, the amount of acetic acid employed in conventional amidosulfamic acid salt formation reaction is significantly higher than that used in the reaction of the present invention. In some embodiments of the present invention, the inventive use of lower amounts of acetic acid requires less amine in the first reaction mixture. Beneficially, the use of lower amounts of amine advantageously reduces raw material cost. In one embodiment, the pH at which the amidosulfamic acid salt formation reaction is conducted may range from 5.5 to 7.0, e.g., from 5.9 to 6.8 or from 6.1 to 6.4. In terms of lower limits, the reaction may be conducted at a pH at least 5.5, e.g., at least 5.7, at least 5.9, or at least 6.1. In terms of upper limits, the reaction may be conducted at a pH less than 7.0, e.g., less than 6.8, or less than 6.4. By conducting the reaction in accordance with the inventive reaction parameters yield, surprisingly and unexpectedly, is improved.

Also, by employing the inventive reaction parameters, the amidosulfamic acid salt that is formed, surprisingly, has improved color properties, e.g., a yellowing index less than 5, e.g., less than 2, less than 1 or less than 0.5, as formed, as determined by ASTM E313. In addition, the acetoacetamide salt that may be subsequently formed from the amidosulfamic acid salt, unexpectedly, may also demonstrate improved color properties, e.g., a yellowing index less than 45, e.g., less than 35, less than 25, or less than 10, as formed. Some conventional processes that operate at pH levels higher than those of the present invention may yield: 1) an amidosulfamic acid salt having a yellowing index greater than 5; and/or 2) an acetoacetamide salt having a yellowing index greater than 45.

Because the inventive amidosulfamic acid salts and acetoacetamide salts have improved color properties, the acesulfame-K, as formed therefrom, may have improved color properties, as compared to conventional acesulfame-K products. In a preferred embodiment, the acesulfame-K, as formed, has a yellowing index less than 5, e.g., less than 3, less than 2, less than 1, or less than 0.5.

In one embodiment, the reaction of the first reaction mixture is conducted at higher temperatures. For example the reaction may be conducted at temperatures greater than 0° C., e.g., greater than 10° C., or greater than 25° C. In one embodiment, the reaction is conducted at temperatures above room temperature. In small-scale batch processes, where the cooling of the reactants and maintenance of lower reaction temperatures is economically feasible, a similar reaction may not be conducted at higher temperatures and instead may be conducted at much lower temperatures, e.g., less than 25° C. or less than 10° C.

In one embodiment, the inventive process is not a small-scale batch process or a laboratory-scale process. For example, the inventive process may yield at least 50 grams of acesulfame-K per batch, e.g., at least 100 grams of acesulfame-K per batch, at least 500 grams of acesulfame-K per batch, at least 1 kilogram of acesulfame-K per batch, or at least 10 kilograms of acesulfame-K per batch. In terms of rates, the inventive process may yield at least 50 grams of acesulfame-K per hour, e.g., at least 100 grams of acesulfame-K per hour, at least 500 grams of acesulfame-K per hour, at least 1 kilogram of acesulfame-K per hour, or at least 10 kilograms of acesulfame-K per hour.

The process further comprises the step of reacting the amidosulfamic acid salt with diketene to form an acetoacetamide salt. In one embodiment, the acetoacetamide salt is conducted in the same reactor as is the amidosulfamic acid salt formation reaction. In a preferred embodiment, the two reactions are conducted in separate reactors. As one example, the reaction product of the amidosulfamic acid salt formation reaction is fed to the acetoacetamide salt formation reactor, wherein the amidosulfamic acid salt is reacted to form the acetoacetamide salt.

In embodiments wherein the two reactions are conducted in the same reactor, the reactions may be conducted at the same pH level.

In embodiments wherein the two reaction are conducted in separate reactors, the acetoacetamide salt formation reaction is conducted at a pH ranging from 5.5 to 7.0, e.g., from 5.9 to 6.8 or from 6.1 to 6.4. In terms of lower limits, the reaction may be conducted at a pH at least 5.5, e.g., at least 5.7, at least 5.9, or at least 6.1. In terms of upper limits, the reaction may be conducted at a pH less than 7.0, e.g., less than 6.8, or less than 6.4. In a preferred embodiment, the pH at which the amidosulfamic acid salt formation reaction is conducted is similar to or the same as that of the acetoacetamide salt formation reaction. In one embodiment, the pH levels of the two reactions may differ from one another.

The process preferably further comprises the step of deriving the acesulfame-K from the acetoacetamide salt. In a preferred embodiment, this deriving involves the following steps: reacting the acetoacetamide salt with a cyclizing agent to form a cyclic sulfur trioxide adduct; hydrolyzing the cyclic sulfur trioxide adduct to form acesulfame-H; and neutralizing the acesulfame-H with potassium hydroxide to form the acesulfame-K.

As discussed, in a first reaction step, sulfamic acid and the amine are reacted to form the amidosulfamic acid salt. An exemplary reaction scheme that employs triethylamine as the amine and yields triethyl ammonium amidosulfamic acid salt is shown below.

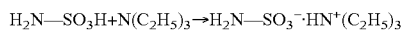

Acetic acid is also present in the first reaction mixture. Acetic acid may react with the amine, e.g., triethylamine, to form a triethylammonium acetate. An exemplary reaction scheme that employs triethylamine as the amine is shown below.

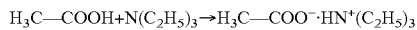

In conventional processes, acetic acid is added to these reactants in higher amounts, e.g., in amounts greater than 1 wt % acetic acid. The addition of acetic acid affects the pH at which the reaction is conducted. The addition of amine to a mixture may increase the pH of the mixture to which the amines are added. Thus, in addition to acetic acid content, the presence of amine in the reaction mixture may also affect the pH at which the reaction is conducted. As such, the amine not only serves as a reactant, but may also adjust the pH of the reaction mixture. In one embodiment, the amine is present in amounts in excess of the stoichiometric amount. In one embodiment, the amidosulfamic acid salt formation reaction is conducted at an amine excess of less than 6 mol %, e.g., less than 5 mol % or less than 3 mol %. In the process of the present invention, however, less acetic acid is used in the first reaction mixture. Accordingly, less amine(s) are required to achieve the desired pH level, as compared to conventional reactions that employ higher amounts of acetic acid.

In one embodiment, the first reaction mixture comprises from 35 wt % to 75 wt % amine(s), e.g., from 45 wt % to 65 wt % or from 50 wt % to 60 wt %, based on the total weight of the first reaction mixture, excluding solvent. In terms of upper limits, the first reaction mixture may comprise less than 75 wt % amine(s), e.g., less than 65 wt % or less than 60 wt %. In terms of lower limits, the first reaction mixture may comprise at least 35 wt % amine(s), e.g., at least 45 wt % or at least 50 wt %. The first reaction mixture may also comprise a solvent. In one embodiment, the first reaction mixture comprises from 45 wt % to 85 wt % solvent, e.g., from 55 wt % to 75 wt % or from 60 wt % to 70 wt %. Exemplary solvents are discussed herein.

In one embodiment, the first reaction mixture has a molar ratio of acetic acid to sulfamic acid that is less than 0.095:1 e.g., less than 0.06:1, less than 0.01:1 or less than 0.001:1. In terms of ranges, the first reaction mixture may have a molar ratio of acetic acid to sulfamic acid in the range of 0.0001:1 to 0.095:1, e.g., from 0.001:1 to 0.06:1.

In one embodiment, a molar ratio of amine(s) to sulfamic acid in the first reaction mixture is greater than 1:1, e.g., greater than 1.02:1 or greater than 1.05:1.

The amine that is employed in this reaction may vary widely. Preferably, the amine comprises triethylamine. In one embodiment, the amine may be selected from the group consisting of trimethylamine, diethylpropylamine, tri-n-propylamine, triisopropylamine, ethyldiisopropylamine, tri-n-butylamine, triisobutylamine, tricyclohexylamine, ethyldicyclohexylamine, N,N-dimethylaniline, N,N-diethylaniline, benzyldimethylamine, pyridine, substituted pyridines such as picoline, lutidine, cholidine or methylethylpyridine, N-methylpiperidine, N-ethylpiperidine, N-methylmorpholine, N,N-dimethylpiperazine, 1,5-diazabicyclo[4.3.0]-non-5-en, 1,8-diazabicyclo-[5.4.0]-undec-7-en, 1,4-diazabicyclooctane, tetramethylhexamethylendiamine, tetramethylethylendiamine, tetramethylpropylendiamine, tetramethylbutylendiamine, 1,2-dimorpholylethan, pentamethyldiethyltriamine, pentaethyldiethylentriamine, pentamethyldipropylentriamine, tetramethyldiaminomethane, tetrapropyldiaminomethane, hexamethyltriethylentetramine, hexamethyltripropylenetetramine, diisobutylentriamine, triisopropylentriamine, and mixtures thereof.

Returning to the acetoacetamide salt formation reaction, amidosulfamic acid salt and an acetoacetylating agent are reacted to form the acetoacetamide salt. Preferably, the acetoacetylating agent is diketene, although other acetoacetylating agents may be employed, either with or without diketene.

In one embodiment, the resultant acetoacetamide salt may correspond to the following formula.

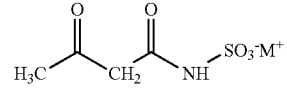

where $M^+$ is an appropriate metal ion,

Preferably, $M^+$ is $Li^+$ or $N^+R_1R_2R_3R_4$. $R_1$, $R_2$, $R_3$ and $R_4$, independently of one another, may be organic radicals or hydrogen, preferably H or $C_1$-$C_8$ alkyl, $C_6$-$C_{10}$ cycloalkyl, aryl and/or aralkyl.

In one embodiment, the total number of carbon atoms in the ammonium ion in the ammonium salts is not more than about 20, in particular not more than about 10.

An exemplary reaction scheme that employs a trialkyl ammonium amidosulfamic acid salt and diketene as reactants and yields an acetoacetamide triethylammonium salt is shown below.

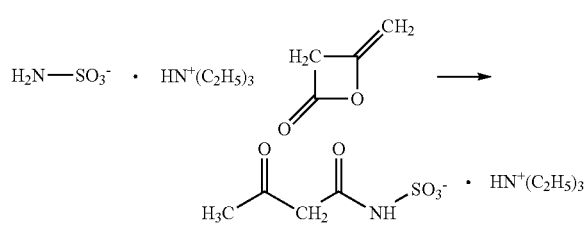

In one embodiment, the reaction is conducted in the presence of a catalyst. The catalyst may vary widely. In some embodiments, the catalyst comprises one or more amines and/or phosphines. Preferably, the catalyst is triethylamine. In addition to triethylamine, other exemplary amine catalysts include the amines listed above with respect the amidosulfamic acid salt formation reaction. Exemplary phosphines include methyldiphenylphosphine, triphenylphosphine, tributylphosphine. In one embodiment, the acetoacetamide salt formation reaction takes place without a catalyst.

In one embodiment wherein the amidosulfamic acid salt formation reaction and the acetoacetamide salt formation reaction are conducted in separate reactors, a second reaction mixture comprises the amidosulfamic acid salt, the diketene, and the catalyst, e.g., triethylamine. Preferably, catalyst from the first reaction is carried through to the reaction mixture of the second reaction. The second reaction mixture is then subjected to conditions effective to form the acetoacetamide salt. Preferably, the second reaction mixture comprises essentially no acetic acid.

In one embodiment, the composition of the second reaction mixture may be similar to that of the first reaction mixture, discussed above. In one embodiment, when the weight of the solvent is taken into consideration in the weight percentage calculation, the second reaction mixture comprises less than 0.157 wt % acetic acid, e.g., less than 0.15 wt %, less than 0.10 wt %, less than 0.8 wt %, or less than 0.5 wt %, based on. In some embodiments, the second reaction mixture may further comprise from 3 wt % to 45 wt % amidosulfamic acid salt, e.g., from 13 wt % to 35 wt % or from 18 wt % to 30 wt %; from 1 wt % to 30 wt % diketene, e.g., from 1 wt % to 20 wt % or from 5 wt % to 15 wt %; and/or from 45 wt % to 85 wt % solvent, e.g., from 55 wt % to 75 wt % or from 60 wt % to 70 wt %. In a preferred embodiment, the reaction product of the amidosulfamic acid salt formation reaction provides the amidosulfamic acid salt component of the second reaction mixture. In addition to the above-mentioned components, the second reaction mixture may further comprise reaction by-products from the first reaction, e.g., (residual) ammonium acetate salt.

In one embodiment, the amount of acetoacetylating agent, e.g., diketene, should be at least equimolar to the reactant amidosulfamic acid salt. In one embodiment, the process may utilize a diketene excess less than 30 mol %, e.g., less than 10 mol %. Greater excesses are also contemplated.

The first and/or second reaction may employ an organic solvent. Suitable inert organic solvents are virtually all organic solvents which do not react in an undesired manner with the starting materials, final products and/or the catalysts in the reaction. The solvents preferably have the ability to dissolve, at least partially, amidosulfamic acid salts. Exemplary organic solvents include halogenated aliphatic hydrocarbons, preferably those having up to 4 carbon atoms such as, for example, methylene chloride, chloroform, 1,2-dichlorethane, trichloroethylene, tetrachloroethylene, trichlorofluoroethylene; aliphatic ketones, preferably those having 3 to 6 carbon atoms such as, for example, acetone, methyl ethyl ketone; aliphatic ethers, preferably cyclic aliphatic ethers having 4 or 5 carbon atoms such as, for example, tetrahydrofuran, dioxane; lower aliphatic carboxylic acids, preferably those having 2 to 6 carbon atoms such as, for example, acetic acid, propionic acid; aliphatic nitriles, preferably acetonitrile; N-alkyl-substituted amides of carbonic acid and lower aliphatic carboxylic acids, preferably amides having up to 5 carbon atoms such as, for example, tetramethylurea, dimethylformamide, dimethylacetamide, N-methylpyrrolidone; aliphatic sulfoxides, preferably dimethyl sulfoxide, and aliphatic sulfones, preferably sulfolane.

Particularly preferred solvents include methylene chloride, 1,2-dichloroethane, acetone, glacial acetic acid and dimethylformamide, with methylene dichloride being particularly preferred. The solvents may be used either alone or in a mixture.

In one embodiment, the reaction is conducted a temperature ranging from −30° C. to 50° C., e.g., from 0° C. to 25° C. The reaction pressure may vary widely. In preferred embodiments, the reaction is carried out at atmospheric pressure. The reaction time may vary widely, preferably ranging from 0.5 hours to 12 hours, e.g., from 1 hour to 10 hours. In embodiment, the reaction is carried out by introducing the amidosulfamic acid salt and metering in the diketene. In one embodiment, the reaction is carried out by introducing diketene and metering in the amidosulfamic acid salt. The reaction may be carried out by introducing the diketene and amidosulfamic acid and metering in the catalyst.

Once formed, the reaction product is preferably subjected to one or more purification steps. For example the solvent may be separated from the reaction product, e.g., via distillation, and the residue (mainly acetoacetamide-N-sulfonate) may be recrystallized from a suitable solvent such as, for example, acetone, methyl acetate or ethanol.

Cyclization, Hydrolyzation and Neutralization

The acetacetamide salt, in preferred embodiments, is reacted with a cyclizing agent to form a cyclic sulfur trioxide adduct. In one embodiment, the cyclization is achieved by using at least an equimolar amount of the cyclizing agent, e.g., sulfur trioxide, which may be dissolved in an inert inorganic or organic solvent. The sulfur trioxide is generally used in a molar excess, e.g., up to a 20 fold excess, or up to a 10 fold excess, based on the acetoacetamide salt. An exemplary cyclization reaction is shown below.

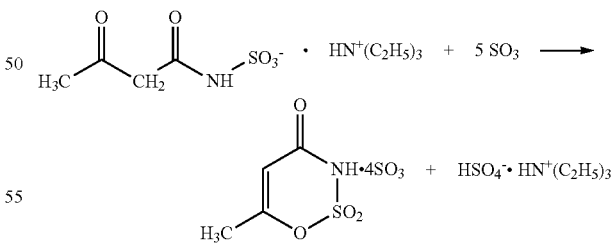

The sulfur trioxide may be added to the reaction mixture either in the solid or the liquid form or by condensing in sulfur trioxide vapor. Preferably, a solution of sulfur trioxide in 1) concentrated sulfuric acid, 2) liquid sulfur dioxide, or 3) an inert organic solvent is used. In one embodiment, the reaction is carried out without a solvent. Suitable inert inorganic or organic solvents are those liquids which do not react in an undesired manner with sulfur trioxide or the starting materials or final products of the reaction. Preferred inorganic solvents include, but are not limited to liquid sulfur dioxide. Preferred organic solvents include, but are not limited to halogenated aliphatic hydrocarbons, preferably having up to 4 carbon atoms, such as, for example, methylene chloride (dichloro methane), chloroform, 1,2-dichloroethane, trichloroethylene, tetrachloroethylene, trichlorofluoroethylene; esters of carbonic acid with lower aliphatic alcohols, preferably with methanol or ethanol; nitroalkanes, preferably having up to 4 carbon atoms, in particular nitromethane; alkyl-substituted pyridines, preferably collidine; and aliphatic sulfones, preferably sulfolane. The processes may employ these solvents alone or in mixtures thereof.

In a preferred embodiment, the same solvent is used in both the acetoacetamide salt formation reaction and the cyclization reaction. As one benefit, the solution obtained in the acetoacetamide salt formation reaction, without isolation of the acetoacetamide salt formation reaction, may be used immediately in the cyclization.

In one embodiment, the reaction temperature for the cyclization reaction ranges from −70° C. to 175° C., e.g., from −40° C. to 10° C. The pressure at which the reaction is conducted may vary widely. In one embodiment, the reaction is conducted at a pressure ranging from 0.01 MPa to 10 MPa, e.g., from 0.1 MPa to 5 MPa. Preferably, the reaction is conducted at atmospheric pressure.

The acetoacetamide salt may be introduced to the reactor and the sulfur trioxide is metered into the reactor. In preferred embodiments, both reactants are simultaneously fed into the reactor. In one embodiment, sulfur trioxide initially introduced into the reactor and the acetoacetamide salt is added. Preferably, at least part of the sulfur trioxide is introduced into the reactor and, either continuously or in portions, acetoacetamide salt and (additional) sulfur trioxide are then metered in.

The cyclic sulfur trioxide adduct may be hydrolyzed and neutralized via conventional means. In cases where methylene chloride is used as the reaction medium, water or ice may be added, e.g., in a molar excess, based on the sulfur trioxide, to the cyclic sulfur trioxide adduct/sulfur trioxide solution. An exemplary hydrolysis reaction scheme is shown below.

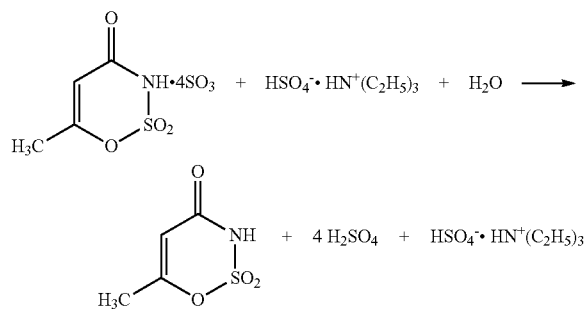

The addition of the water leads to a phase separation. The sweetener acid, acesulfame-H (6-methyl-3,4-dihydro-1,2,3-oxathiazin-4one 2,2-dioxide), which is formed via the hydrolysis, is present in the organic phase.

After the addition of water, the reaction solvent may be removed by distillation, and the acesulfame-H that remains in the organic phase may be extracted with a more suitable solvent. Suitable solvents are those which are sufficiently stable towards sulfuric acid and which have a satisfactory dissolving capacity. Other suitable solvents include esters of carbonic acid such as, for example dimethyl carbonate, diethyl carbonate and ethylene carbonate, or esters of organic monocarboxylic acids such as, for example, isopropyl formate and isobutyl formate, ethyl acetate, isopropyl acetate, butyl acetate, isobutyl acetate and neopentyl acetate, or esters of dicarboxylic acids or amides which are immiscible with water, such as, for example, tetrabutylurea, are suitable. Isopropyl acetate and isobutyl acetate are particularly preferred.

The combined organic phases are dried with, for example, $Na_2SO_4$, and are evaporated. Any sulfuric acid which has been carried over in the extraction can be removed by appropriate addition of aqueous alkali to the organic phase. For this purpose, dilute aqueous alkali may be added to the organic phase until the pH reached in the aqueous phase corresponds to that of pure 6-methyl-3,4-dihydro1,2,3-oxathiazin-4-one 2,2-dioxide at the same concentration in the same two-phase system of extracting agent and water.

The neutralization of the acesulfame-H yields a non-toxic salt of acesulfame-H, e.g., acesulfame-K. In one embodiment, the neutralization is carried out by reacting the acesulfame-H with an appropriate base, e.g., potassium hydroxide. Other suitable bases include, for example, KOH, $KHCO_3$, $K_2CO_3$, potassium alcoholates. An exemplary reaction scheme using potassium hydroxide as a neutralizing agent is shown below.

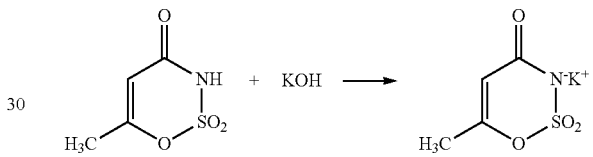

In one embodiment, the acesulfame-H may be neutralized and extracted directly from the purified organic extraction phase using an aqueous potassium base. The acesulfame-K then precipitates out, where appropriate after evaporation of the solution, in the crystalline form, and it can also be recrystallized for purification.

FIG. 1 shows exemplary acesulfame-K process 100, which is in accordance with the present invention. Process 100 comprises amidosufamic acid salt formation reactor 102 and acetoacetamide salt formation reactor 104. Although FIG. 1 shows separate reactors for the two intermediate formation reactions, other configurations, e.g., a one reactor process, are within the contemplation of the present invention. Sulfamic acid is fed to amidosufamic acid salt formation reactor 102 via sulfamic acid feed 106. Amine(s), preferably triethylamine, are fed to amidosufamic acid salt formation reactor 102 via amine feed line 108. In addition to sulfamic acid and amine(s), acetic acid is also fed to amidosufamic acid salt formation reactor 102 (via line 110 ). The resultant reaction mixture in amidosufamic acid salt formation reactor 102 is as discussed above. In amidosufamic acid salt formation reactor 102, the sulfamic acid and the amine (in the presence of the acetic acid) are reacted to yield a crude amidosufamic acid salt composition, which exits reactor 102 via line 112. By controlling the feed rate of the acetic acid and/or the amide(s), the reaction in amidosufamic acid salt formation reactor 102 is maintained at the inventive pH levels. Although not shown, a reaction solvent, e.g., methylene dichloride may also be present in amidosufamic acid salt formation reactor 102.

The crude amidosufamic acid salt composition in line 112 is directed to acetoacetamide salt formation reactor 104. Diketene is fed to acetoacetamide salt formation reactor 104 via line 114. The resultant reaction mixture in acetoacetamide salt formation reactor 104 is as discussed above. In acetoacetamide salt formation reactor 104, the amidosufamic acid salt and the diketene are reacted to yield a crude acetoacetomide salt composition, which exits reactor 104 via line 118. By controlling the feed rate of the amide(s), the reaction in acetoacetamide salt formation reactor 104 is maintained at the inventive pH levels. Although not shown, methylene dichloride may also be present in acetoacetamide salt formation reactor 104.

The crude acetoacetomide salt composition is directed to cyclization reactor 120. Sulfur trioxide is also fed to cyclization reactor 120 (via line 122). In cyclization reactor 120, the acetoacetamide salt in line 118 is cyclized and a cyclic sulfur trioxide adduct stream, which exits via line 124.

Line 124, which contains the cyclic sulfur trioxide adduct, is directed to hydrolysis reactor 126. Water is fed to hydrolysis reactor 126 via water feed 128. In hydrolysis reactor 126, the cyclic sulfur trioxide adduct is hydrolyzed to yield a crude acesulfame-H stream, which exits hydrolysis reactor 126 via line 130 and is directed to phase separation unit 132. Phase separation unit 132 separates the contents of line 130 into an organic phase 134 and an aqueous phase 136. Organic phase 134 comprises a major amount of the acesulfame-H in line 130 as well as solvent, e.g., methylene chloride. Aqueous phase 136 exits via line 137 and comprises triethylammonium sulfate, and optionally sulfuric acid and minor amounts of acesulfame-H. This phase may be further purified to separate and/or recover the acesulfame-H and/or the triethylammonium sulfate. The recovered acesulfame-H may be combined with the acesulfame from the organic phase (not shown).

The organic phase exits phase separation unit 132 and is directed to extraction column 138 (via line 140). Water is fed to extraction column 138 via water feed 142. The water extracts residual sulfates from the contents of line 140 and a purified acesulfame-H stream exits extraction column 138 via line 144. The extracted sulfates exit extraction column 138 via line 145.

Line 144 is directed to neutralization unit 146. Potassium hydroxide is also fed to neutralization unit 146 (via line 148). The potassium hydroxide neutralizes the acesulfame-H to yield a crude acesulfame-K product, which exits neutralization unit 146 via line 150. The crude acesulfame-K product stream comprises acesulfame-K, methylene dichloride, water, and potassium hydroxide. The crude acesulfame-K product stream in line 150 may be directed to further processing to recover purified acesulfame-K, which is shown exiting via stream 152. In addition to the purified acesulfame-K, methylene dichloride and potassium hydroxide may be separated from the crude acesulfame-K product stream, as shown by stream 154. The contents of stream 154 may be recovered and/or recycled to the process.

While the invention has been described in detail, modifications within the spirit and scope of the invention will be readily apparent to those of skill in the art. In view of the foregoing discussion, relevant knowledge in the art and references discussed above in connection with the Background and Detailed Description, the disclosures of which are all incorporated herein by reference. In addition, it should be understood that aspects of the invention and portions of various embodiments and various features recited below and/or in the appended claims may be combined or interchanged either in whole or in part. In the foregoing descriptions of the various embodiments, those embodiments which refer to another embodiment may be appropriately combined with other embodiments as will be appreciated by one of skill in the art. Furthermore, those of ordinary skill in the art will appreciate that the foregoing description is by way of example only, and is not intended to limit the invention.

We claim:

1. A process for producing acesulfame potassium, the process comprising the steps of:
    (a) reacting a first reaction mixture comprising:
        sulfamic acid,
        an amine, and
        from 1 wppm to 1 wt % wppm acetic acid
    to form an amidosulfamic acid salt;
    (b) reacting the amidosulfamic acid salt with diketene to form an acetoacetamide salt;
    (c) deriving the acesulfame potassium from the acetoacetamide salt,
    wherein a molar ratio of acetic acid to sulfamic acid in the first reaction mixture is less than 0.095:1.

2. The process of claim 1, wherein step (c) comprises:
    reacting the acetoacetamide salt with a cyclizing agent to form a cyclic sulfur trioxide adduct; and
    deriving the acesulfame potassium composition from the cyclic sulfur trioxide adduct.

3. The process of claim 2, wherein the deriving comprises:
    hydrolyzing the cyclic sulfur trioxide adduct to form acesulfame-H; and
    neutralizing the acesulfame-H with potassium hydroxide to form the potassium acesulfame.

4. The process of claim 1, wherein the amine comprises triethylamine.

5. The process of claim 1, wherein the reaction in step (a) is conducted at an amine excess of less than 6 mol %.

6. The process of claim 1, wherein the amidosulfamic acid salt has a yellowing index less than 5 and/or the acetoacetamide salt has a yellowing index less than 45.

7. The process of claim 1, wherein a molar ratio of amine to sulfamic acid in the first reaction mixture is less than 1.06:1.

8. The process of claim 1, wherein the process does not comprise an acetic acid removal step.

9. The process of claim 1, wherein step (b) comprises:
    contacting the amidosulfamic acid salt and diketene to form a second reaction mixture; and
    reacting the second reaction mixture to form the acetoacetamide salt.

10. A process for producing acesulfame potassium, the process comprising the steps of:
    (a) reacting a first reaction mixture comprising:
        sulfamic acid,
        an amine, and
        from 1 wppm to 1 wt % wppm acetic acid
    to form an amidosulfamic acid salt;
    (b) reacting the amidosulfamic acid salt with diketene to form an acetoacetamide salt;
    (c) deriving the acesulfame potassium from the acetoacetamide salt,
    wherein the acesulfame potassium has a yellowing index less than 5.

11. A process for producing acesulfame potassium, the process comprising the steps of:
    (a) reacting a first reaction mixture comprising:
        sulfamic acid,
        an amine, and
        from 1 wppm to 1 wt % wppm acetic acid
    to form an amidosulfamic acid salt;
    (b) reacting the amidosulfamic acid salt with diketene to form an acetoacetamide salt;
    (c) deriving the acesulfame potassium from the acetoacetamide salt, wherein a molar ratio of amine to sulfamic acid in the first reaction mixture is less than 1.06:1.

* * * * *